United States Patent [19]
Michelson

[11] Patent Number: 5,785,710
[45] Date of Patent: Jul. 28, 1998

[54] INTERBODY SPINAL FUSION IMPLANTS

[75] Inventor: Gary Karlin Michelson, Venice, Calif.

[73] Assignee: Sofamor Danek Group, Inc., Memphis, Tenn.

[21] Appl. No.: 474,478

[22] Filed: Jun. 7, 1995

Related U.S. Application Data

[60] Division of Ser. No. 390,131, Feb. 17, 1995, Pat. No. 5,593,409, which is a continuation-in-part of Ser. No. 968,240, Oct. 29, 1992, which is a continuation of Ser. No. 698,674, May 10, 1991, abandoned, which is a division of Ser. No. 205,935, Jun. 13, 1988, Pat. No. 5,015,247, and a continuation-in-part of Ser. No. 23,926, Jun. 3, 1994, Pat. No. Des. 377,096.

[51] Int. Cl.$^6$ .................................................. A61B 17/56
[52] U.S. Cl. .................................................. 606/61; 623/17
[58] Field of Search .................. 606/60, 61, 72–77; 623/16, 17, 18, 66

[56] References Cited

U.S. PATENT DOCUMENTS

| | | | |
|---|---|---|---|
| 4,501,269 | 2/1985 | Bagby | 606/61 |
| 4,743,256 | 5/1988 | Brantigan | 623/17 |
| 4,834,757 | 5/1989 | Brantigan | 623/17 |
| 4,878,915 | 11/1989 | Brantigan | 623/17 |
| 5,015,247 | 5/1991 | Michelson | 606/61 |
| 5,055,104 | 10/1991 | Ray | 606/61 |
| 5,425,772 | 6/1995 | Brantigan | 623/17 |

*Primary Examiner*—Michael A. Brown
*Attorney, Agent, or Firm*—Woodard, Emhardt, Naughton, Moriarity & McNett

[57] ABSTRACT

The present invention discloses a spinal fusion implant that is at least partially cylindrical, made of material appropriate for human implantation and having preferably, but not necessarily, one closed end and one end capable of being closed, such that an internal chamber can be filled and hold any natural or artificial osteoconductive, osteoinductive, osteogenic, or other fusion enhancing material. The partially cylindrical implant directly participates and is incorporated in the ensuing fusion. In the preferred embodiment, the implant of the present invention relies on surface roughenings of the outer surface to enhance its stability and resist dislodgement from within the disc space between two adjacent vertebrae. The implant of the present invention incorporates at its rear end, an engagement means to facilitate insertion or extraction of the implant. The implant may be filled with, coated with, and/or composed of, fusion promoting substances. Finally, the implant of the present invention does not require rotation for its insertion and can be seated by linear advancement.

13 Claims, 11 Drawing Sheets

INTERBODY SPINAL FUSION IMPLANTS

RELATED APPLICATIONS

This application is a division of application Ser. No. 08/390,131, filed Feb. 17, 1995 now U.S. Pat. No. 5,573,409 which is a continuation in part of copending application Ser. No. 07/968,240 filed on Oct. 29, 1992 which is a continuation of application Ser. No. 07/698,674 filed on May 10, 1991, now abandoned, which is a division of application Ser. No. 07/205,935 filed on Jun. 13, 1988, now U.S. Pat. No. 5,015,247, issued on May 14, 1991. This Application is also a continuation in part of design patent application Ser. No. 29/023,926 filed on Jun. 3, 1994 now U.S. Pat. No. D. 377,096.

BACKGROUND

1. Field of the Invention

The present invention relates to artificial spinal fusion implants to be placed across the intervertebral space left after the removal of a damaged spinal disco and in particular to an improved, at least partially cylindrical, spinal fusion implant for implantation where two threaded cylindrical implants of requisite height would not fit within the transverse width of the spine.

2. Description of the Related Art

In the past, Cloward, Wilterberger, Crock, Viche, Bagby, Brantigan, Michelson and others have taught various methods involving the drilling of holes across the disc space between two adjacent vertebrae of the spine for the purpose of causing an interbody spinal fusion. Cloward taught placing a dowel of bone within that drilled hole for the purpose of bridging the defect and to be incorporated into the fusion. Viche taught the threading of that bone dowel. Bagby taught the placing of the bone graft into a metal bucket otherwise smooth on its surface, except for rows of radially placed holes communicative to the interior of the basket and to the bone graft. The Bagby device was disclosed as capable of being used in a horse. Brantigan taught the use of inert blocks preferably made of metal and having that metal at its external surface imitate the porosity of bone. Brantigan theorized that the bone dowel could be replaced entirely with a metal plug, that, while not itself active in the fusion, would nevertheless serve to support the vertebrae from within the disc space while allowing fusion to occur around it.

U.S. Pat. No. 3,844,601 issued to Ma et al. on Nov. 19, 1974, teaches a method and instrumentation for preparing rectangular spaces across the disc space into the adjacent vertebrae and for preparing a rectangular graft of the bone itself that is inserted in the rectangular spaces.

U.S. Pat. No. 4,743,256 issued to Brantigan on May 10, 1988 teaches the use of an inert artificial spacer in the shape of a rectangle in place of using a rectangular bone graft as taught by Ma et al.

U.S. Pat. No. 4,878,915 issued to Brantigan on Nov. 7, 1989, teaches the use of fully cylindrical inert implants for use in interbody spinal fusion. Such implants do not participate in the bone fusion process but act as inert spacers and allow for the growth of bone to the outer surfaces of the implants.

U.S. Pat. No. 4,834,757 issued to Brantigan on May 30, 1989, teaches a rectangular shaped, hollow spinal fusion implant for use in lieu of a rectangular bone graft or Brantigan's earlier artificial inert spacer.

U.S. Pat. No. 5,015,247 issued to Michelson on May 14, 1991, teaches the use of a thin-walled, highly perforated, threaded, hollow cylindrical implant closed or closable at both ends, so as to be compressably loaded with bone or other fusion promoting materials. Additionally, the Michelson device may then be coated with a bone production inducing chemical such as hydroxyapatite. The Michelson patent, also discloses an improved method of drilling holes across the disc space and into the two adjacent vertebrae and safely installing cylindrical implants such that the entire surgical procedure may be conducted through a hollow cylindrical tube. The hollow cylindrical tube may be left in place throughout the surgical procedure and serves to hold the adjacent vertebrae in place relative to each other, permits the guarded drilling of the holes across the disc space, and permits the insertion of the implant through that same tube into the hole drilled across the disc space and into the adjacent vertebrae.

As regards this method of performing interbody spinal fusion using essentially cylindrical threaded implants, a special problem arises (see FIG. 1) when an attempt is made to place two cylindrical implants (considered to be the preferred number as it is a much more stable construct and has more surface area than a single implant placed centrally) side-by-side across a disc space and into the two adjacent vertebrae where the height of the disc space is such that it requires an implant of a diameter so large to penetrate into and significantly engage each of the adjacent vertebrae that it is no longer possible to place two such implants side-by-side and to still have them contained within the transverse width of the spine. If an attempt is made to remedy the problem by using smaller diameter implants placed side-by-side such that both would then be able to fit within the transverse width of the spine, then the implants would be of insufficient height to adequately engage the bone. If an attempt is made to remedy the problem by abandoning the side-by-side double implant construct in favor of a single, centrally placed implant, then where the implant is sufficiently large enough to occupy a sufficient portion of the transverse width of the disc space to promote firm stability, its vertical height and excursion into the vertebrae would be so severe that if any two consecutive disc spaces were to be operated upon, the vertebrae in between would be cut in half.

U.S. Pat. No. 5,055,104 issued to Ray on Oct. 8, 1991 ("Ray Patent") discloses an implant comprising a helical coil without wall members that is assembled after the coils are placed in the disc space between the vertebrae, which supposedly can then be removed after the vertebrae have become fused together. The Ray implant is defective and unworkable in that it is incapable of being used in the manner in which it is described as it is not possible to insert into hard bone an isolated helical coil without any wall members to support such a coil, which coil would be analogous structurally to a slinky. (See Ray Patent, FIGS. 1 and 7). Further, the Ray implant is unduly complex, because it would require the difficult, if not impossible, task of assembly within the disc space. FIG. 3 of the Ray patent clearly reveals that Ray does not teach the use of a truncated cylindrical implant, but merely teaches the use of a truncated, helical coil appearing as a sharpened spring totally lacking any wall member which could be considered cylindrical. Therefore, Ray teaches only the use of an isolated thread which can only be inserted by rotation and cannot be linearly advanced.

If the overwhelming obstacles of the impossibility of inserting an isolated thread without wall members and the problem of the assembly within the disc space could be overcome, then the Ray implant would still be unsafe for its intended purpose as it would be at high risk of spontaneous disassembly and mechanical failure. Further, there would be insufficient room to safely rotate such a device for insertion as it is the very lack of such room that requires the use of a device having a decreased transverse width.

There is therefore, the need for a spinal fusion implant that is capable of being inserted into a hole drilled across the disc space between two adjacent vertebrae and partially into the two adjacent vertebrae such that the spinal fusion implant is capable of fitting within the transverse width of the spine when placed side-by-side next to a second of its kind.

SUMMARY OF THE PRESENT INVENTION

The present invention is an improved interbody spinal fusion implant that is capable of being inserted into a hole drilled across the disc space between two adjacent vertebrae and into the two adjacent vertebrae such that the spinal fusion implant is capable of fitting within the transverse width of the spine when placed side-by-side next to a second of its kind. The spinal fusion implant of the present invention comprises a thin-wall, multi-perforate, cylinder or partial cylinder, made of material appropriate for human implantation and having preferably, but not necessarily, one closed end and one end capable of being closed, such that an internal chamber can be filled and hold any natural or artificial osteoconductive, osteoinductive, osteogenic, or other fusion enhancing material. The spinal fusion implant of the present invention relies on rougheneings of the outer surface to enhance its stability. Depending on the dimension of the transverse width of the spine in which the spinal fusion implant is being inserted, the spinal fusion implant of the present invention may have one or more flat sides to reduce the width of the spinal fusion implant. The spinal fusion implant of the present invention incorporates at its rear end, an engagement means to facilitate insertion or extraction of the implant, preferably at its rear end. The implant of the present invention may be made of, filled with and/or coated with fusion promoting substances. Further, the spinal fusion implant of the present invention does not require rotation for its insertion and can be seated by linear advancement.

The spinal fusion implant of the present invention is generally effective, and is safer and more effective than the cylindrical implants of the prior art for the special instance when it is desirable to insert two implants side-by-side into cylindrically prepared channels, and where the height of the disc space between two adjacent vertebrae is so great relative to the transverse width of the spine, that two implants of the requisite height will not fit within the transverse width of the spine. Prior art has taught those knowledgeable in the art of spinal surgery, that the likelihood of obtaining a spinal fusion is proportionate to three factors: 1) the surface area of the implant 2) the quality and quantity of the graft material and 3) the stability of the fusion construct. The spinal fusion implant of the present invention increases each of these three factors by making it possible to use two implants side-by-side across a disc space that would otherwise lack sufficient width to accept more than one.

The spinal fusion implant of the present invention is more efficacious than the prior art on an individual implant basis for the following reasons:

1. Increased surface area. The spinal fusion implant of the present invention, because of its surface rougheneings has greater surface area for engaging the adjacent vertebrae than an implant with smooth external surfaces. The presence or absence of holes does not materially affect this, so far as the holes are filled with material effectively contributing to the area of contact at the surface. The arced portions of the partially cylindrical implant of the present invention are in contact with the adjacent vertebrae and provide a greater surface area than is possible with a flat portion from a non-cylindrical implant.

2. The quantity and quality of graft material presented. As the spinal fusion implant of the present invention is not screwed in, it need not be constructed to resist the torquing therewith associated. Thus, the implant of the present invention may be thinner walled and thereby, for a given diameter, have greater internal volume. The spinal fusion implant, of the present invention has arced portions making the implant stronger in compression than an implant lacking upper and lower curved supporting surfaces such that the wall of the implant can be relatively thinner than such implants. A thinner wall is easier for bone to grow through. Also, the interpore bridges may be smaller allowing for greater porosity and thereby greater exposure to the internal graft material. Further, the spinal fusion implant of the present invention may be constructed of and/or coated with, and/or loaded with a variety of materials and/or chemical substrates known to actively participate in the bone fusion process. As the spinal fusion implant of the present invention offers greater surface area, and greater internal volume for its outside diameter, it offers the opportunity for presenting a greater surface area and volume of these fusion materials.

3. The implant of the present invention offers greater stability than the prior art implants. The least stable implants are the implants lacking surface rougheneings. Surface holes increase implant stability by increasing the interference of the implant to the opposed surfaces. The spinal fusion implant of the present invention is a further improvement over the prior art in that the surface rougheneings of the spinal fusion implant of the present invention resist motion in all directions. Further, all implants are subject to the possibility of backing out, by retracing the path by which they were inserted. However, the spinal fusion implant of the present invention can have a surface configured to urge the spinal fusion implant forward as to offer increased resistance against such undesirable backward migration. Further, the arced portions of the implant of the present invention provide a greater support area to better distribute the compression forces through the vertebrae.

The spinal fusion implant of the present invention is easier to use as it occupies less space, does not require pretapping, and can be inserted without the need to rotate an instrument within the closed confines of the spinal wound. Further, the spinal fusion implant of the present invention is easier to insert than implants lacking upper and lower curved supporting surfaces that are arcs of the same circle and which implants are to be inserted across the disc space and into the adjacent vertebrae as it is easier to prepare a round hole than a square hole, as a round hole can be drilled in a single step.

OBJECTS OF THE PRESENT INVENTION

It is an object of the present invention to provide an improved interbody spinal fusion implant such that it is possible to place two such implants side-by-side across a disc space and into two adjacent vertebrae in close approximation to each other and within the transverse width of the spine, where the transverse width of the spine would have otherwise been insufficient relative to the required implant height to have allowed for the accommodation of two prior art cylindrical threaded implants.

It is another object of the present invention to provide a spinal fusion implant that is easier to insert, and does not require tapping prior to implantation.

It is yet another object of the present invention to provide a spinal fusion implant that is safer, in which there is no need to run sharp threads near delicate structures.

It is still another object of the present invention to provide a spinal fusion implant that is faster to implant between adjacent vertebrae via linear advancement as opposed to rotational advancement.

It is yet another object of the present invention to provide a method for implanting partially cylindrical implants having at least one flat side.

These and other objects of the present invention will be apparent from a review of the accompanying drawings and the following detailed description of the drawings.

DETAILED DESCRIPTION OF THE DRAWINGS

The Previous Devices

Figure 1:
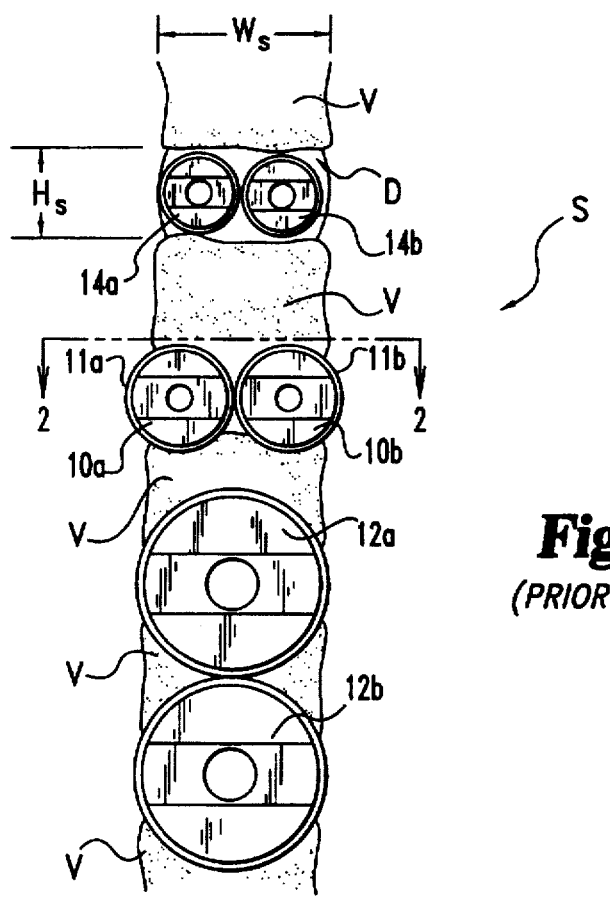
FIG. 1 is a diagrammatic representation of a segment of the human spinal column comprising several vertebrae with various cylindrical threaded implants inserted across the disc space and into the two adjacent vertebrae to illustrate the problems encountered by those implants.

Referring to FIG. 1, a diagrammatic representation of a segment of the human spinal column generally referred to by the letter S is shown. The segment of the spinal column S comprises several vertebrae V and a disc space D between two adjacent vertebrae V. Various cylindrical threaded spinal fusion implants, each having different diameters, are shown inserted across the disc space D.

When the height $H_S$ of the disc space D is so large that two cylindrical implants, such as spinal fusion implants 10a and 10b, each having a sufficient diameter to cross the disc space D and sufficiently engage into the bone of adjacent vertebrae V, are placed across the disc space D, the combined overall width of the two spinal implants 10a and 10b exceeds the transverse width $W_S$ of the spinal column S. As a result, a portion of each implant 10a and 10b protrudes from the sides of the spinal column S and could cause severe and perhaps mortal damage to the patient as delicate and vital structures lie adjacent to that area of the spinal column S such that the use of two cylindrical spinal fusion implants 10a and 10b would not be desirable.

If instead of two spinal fusion implants 10a and 10b, a single implant, such as spinal fusion implant 12a were to be used having a sufficient diameter to provide for stability and fusion, then the implant would penetrate deeply into the adjacent vertebrae V. The spinal fusion implant 12a would have a diameter that is significantly greater than the height $H_S$ of the disc space D, such that the vertebrae V would have to be substantially bored out to accommodate the large diameter of the spinal fusion implant 12a. As a result, a large part of the vertebrae V would be removed, and thus the overall structural integrity of the vertebrae V would be substantially weakened. This is especially a problem when a second spinal fusion implant 12b identical to spinal fusion implant 12b is placed across disc space D on the other side of the same vertebrae V such that two spinal fusion implants 12a and 12b are placed across the disc spaces D on either side of the vertebrae V. As a result, the vertebra V is cleaved into a "butterfly" configuration as shown in FIG. 1, and the structural integrity and strength of the vertebrae V is further diminished such that the effectiveness of the spinal fusion process is substantially reduced, and the vertebrae V are at high risk of devascularization and fracture.

Conversely, if two cylindrical implants such as spinal fusion implants 14a and 14b, each having a sufficiently sized diameter such that when placed side-by-side in the disc space D, the combined overall width of the spinal fusion implants 14a and 14b just fills the transverse width $W_S$ of the spinal column S, the diameter of each of the spinal fusion implants 14a and 14b will not be sufficient to cross the disc space D to engage the vertebrae V. Therefore, while the spinal fusion implants 14a and 14b will not protrude from the sides of the spinal column S, the spinal fusion implants 14a and 14b cannot reach and engage the bone of the vertebrae V and thus cannot function to stabilize the adjacent vertebrae V.

Figure 2:
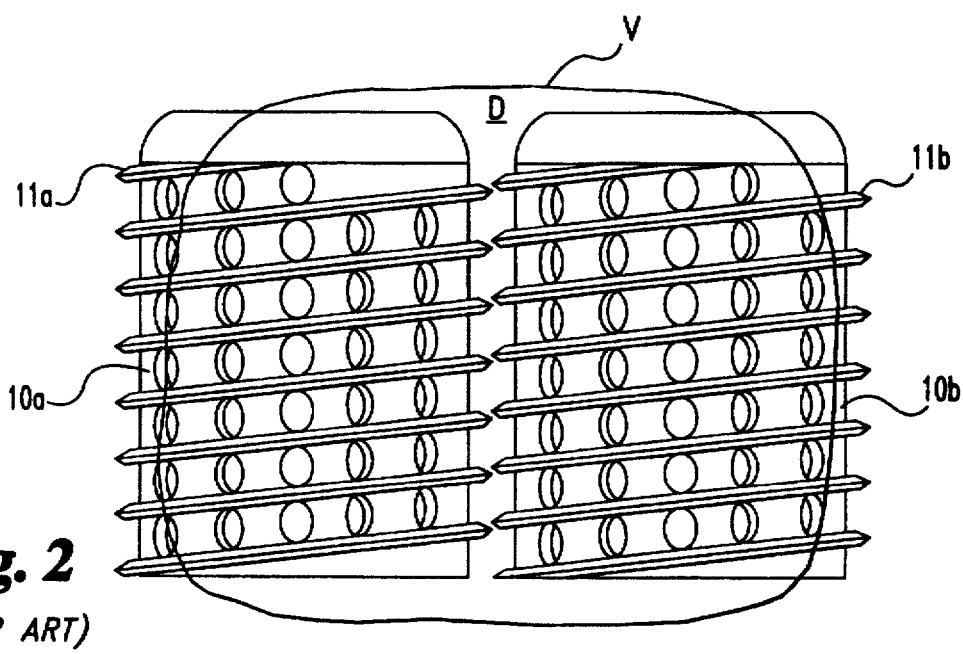
FIG. 2 is a top plan view along lines 2—2 of FIG. 1 with the top vertebrae removed, of two cylindrical threaded implants illustrating the minimum distance possible between the two threaded implants when placed beside each other across the disc space.
Figure 3:
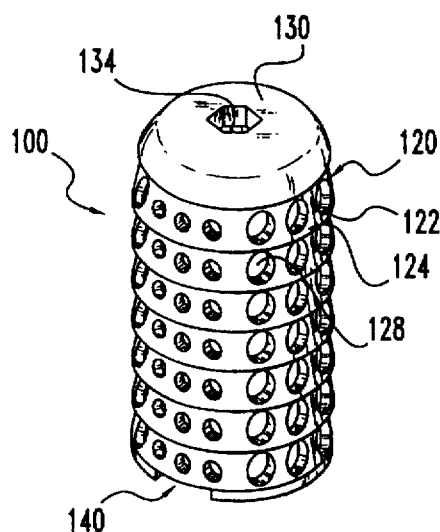
FIG. 3 is a perspective side view of an embodiment of the spinal fusion implant of the present invention having surface roughenings in the form of ratchetings.

Referring to FIG. 2, a top plan view, taken along line 2—2 of FIG. 1 with the upper vertebrae V removed, of two cylindrical threaded implants 10a and 10b placed across the disc space D is shown. The threaded implants 10a and 10b have an external thread 11a and 11b which must have a minimum height that is proportional to the size of the threaded implant to be effective. The thread 11a and 11b of the threaded implants 10a and 10b converts torque to linear motion, such that the threads 11a and 11b need to be of a sufficient height to overcome the resistance of the material, such as bone, in which the threaded implants 10a and 10b are being inserted, such resistance being proportional to the surface area and diameter of each of threaded implant 10a and 10b. Thus, the difference between the major diameter (including the threads) and the root diameter (minus the threads) of each threaded implant 10a and 10b is such that when two threaded implants 10a and 10b are implanted across the disc space D and into the adjacent vertebrae V, there must be a minimum distance between the two threaded implants 10a and 10b to allow for the height of the threads 11a and 11b. This would be true even if the threads 11a and 11b were interdigitated, the threaded implants 10a and 10b would still be offset by at least the height of the thread of at least one of the threaded implants 10a and 10b. Such a minimum distance between the two threaded implants 10a and 10b increases the combined overall width of the two threaded implants 10a and 10b when inserted.

Therefore, in order for a cylindrical spinal fusion implant to be used in the spinal fusion process where the height $H_S$ of the disc space D between two adjacent vertebrae V is large relative to its width $W_S$, it is necessary to have an implant that can be implanted adjacent to a second of its kind in closer contact than is possible with threaded implants, while still providing for an implant surface that will provide mechanical stability in engagement to the adjacent vertebrae V. The use of a cylindrical implant is desirable as it is easy to prepare the recipient site by drilling a cylindrical hole across the disc space D and into the adjacent vertebrae V. The curved surface of the cylindrical holes drilled into the vertebrae V have increased surface area compared to a flat surface and also provides for the possibility of tight congruency when the cylindrical hole is fitted with an implant having corresponding cylindrical portions of matched diameter.

The Present Invention

Referring to FIGS. 3–10, an embodiment of the spinal fusion implant of the present invention, is shown and generally referred to by the numeral 100. The spinal fusion implant 100 has a substantially cylindrical configuration having a thin outer wall 112 surrounding an internal chamber 114 and a longitudinal central axis L. The exterior of the spinal fusion implant 100 comprises surface roughenings that provide a surface suitable for engaging the vertebrae V to stabilize the spinal fusion implant 100 across the disc space D and into the adjacent vertebrae V once surgically implanted. In one embodiment of the spinal fusion implant 100, the surface roughenings comprise a plurality of ratchetings 120 along the circumference of said spinal fusion implant. Each of the plurality of ratchetings 120 has a bone engaging edge 122 and an angled segment 124.

Each of the plurality of ratchetings 120 has a height that is substantially less than the height of a requisite thread for a cylindrical threaded implant of the same size. As a thread is a simple device for converting torque to linear advancement, the requisite height of the thread is proportional to the surface area and diameter of the implant and must be sufficient to pull a cylindrical implant having a diameter sufficient to cross the disc space D through a material as dense as bone. In contrast, the ratchetings 120 have a height that is significantly less than the requisite height of a thread of a same sized threaded implant since the spinal fusion implant 100 is implanted across the disc space D and into the adjacent vertebrae V by linear advancement. The spinal fusion implant 100 may be pushed into the cylindrical disc space D by direct, linear advancement since it requires no thread to pull it forward through the spine. As no torque is required to advance the spinal fusion implant 100 there is no minimum requisite height of the surface roughenings. The only surface feature necessary is that which gives the spinal fusion implant 100 stability once implanted.

Moreover, the ratchetings 120 may face in one direction, the direction in which the spinal fusion implant 100 is inserted, and function to prevent the spinal fusion implant 100 from backing out of the disc space D in a direction opposite to the direction of insertion once inserted between the two adjacent vertebrae V. The ratchetings 120 urge the spinal fusion implant 100 forward against the unremoved bone of the vertebrae V. Since implants generally want to back out along the same path in which they are inserted, such as repeated movement of the patient's body over time and which would cause some other design of implant to come loose (e.g. cause a threaded cylindrical implant to possibly unscrew), the ratchetings 120 tend to urge the spinal fusion implant 100 forward against the solid unremoved bone further resisting dislodgement and controlling motion resulting in an exceedingly stable implantation.

The bone engaging edges 122 of the ratchetings 120 that have a height at a highest point measured from the root diameter of the spinal fusion implant 100 that is approximately 0.35 mm. In this manner the spinal fusion implant 100 may be placed beside a second of its kind at a distance of approximately 0.7 mm apart or if offset even closer, substantially reducing the combined overall width of the two spinal fusion implants 100 once surgically implanted. The ratchetings 120 may have a height in the range of 0.25–1.5 mm, with the preferred height range being 0.35–0.75 mm.

Figure 5:
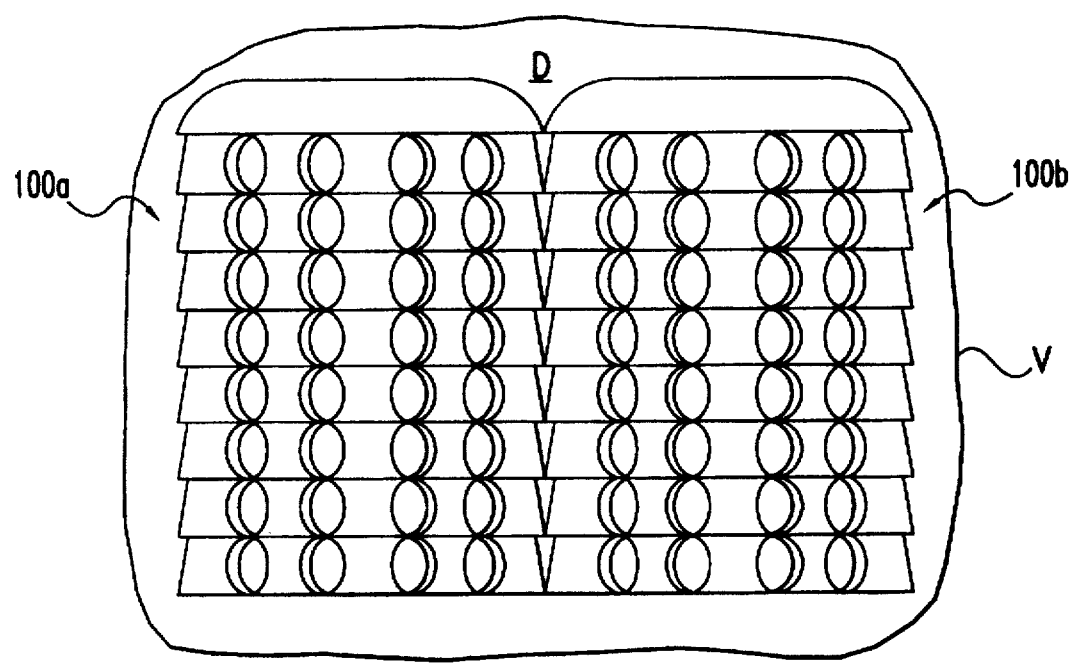
FIG. 5 is a top plan view of two spinal fusion implants of FIG. 3 illustrating the minimum distance possible between the two implants when placed beside each other across the disc space.

Referring to FIG. 5, two spinal fusion implants 100a and 100b are shown inserted across the disc space D having the same dimensions of the disc space D shown in FIG. 2. The two spinal fusion implants 100a and 100b have a decreased overall combined width when compared to two threaded spinal fusion implants placed side by side previously described and illustrated in FIG. 2. The decreased combined overall width of the two spinal fusion implants 100a and 100b is the difference between the root and major diameters of the spinal fusion implants 100a and 100b and is achieved by utilizing surface roughenings such as ratchetings 120 for stability. The surface roughenings allow the two spinal fusion implants 100a and 100b to come into considerably closer approximation to one another and require less total transverse width for their insertion than is possible for two threaded cylindrical implants having identical root diameters because of the requisite thread height of such threaded implants. Reducing the offset between implants allows for the uses of larger diameter implants which can then still fit within the transverse width $W_S$ of the spinal column and achieve more substantial engagement into the adjacent vertebrae V.

Figure 7:
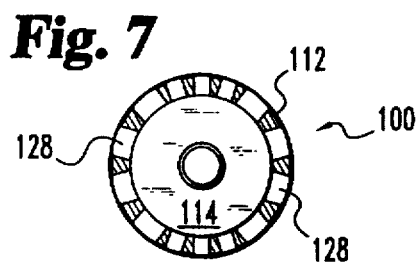
FIG. 7 is a cross sectional view along lines 7—7 of the spinal fusion implant of FIG. 6.
Figure 6:
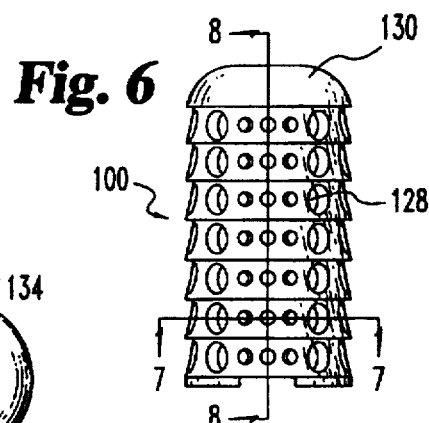
FIG. 6 is a second side elevational view of the spinal fusion implant of FIG. 3.

Referring to FIG. 7, a cross section of the spinal fusion implant 100 is shown wherein the wall 112 has openings 128 passing therethrough to communicate with the internal chamber 114. The internal chamber 114 may be filled with bone material or any natural or artificial bone growth material or fusion promoting material such that bone growth occurs from the vertebrae V through the openings 128 to the material within internal chamber 114. While the openings 128 have been shown in the drawings as being circular, it is appreciated that the openings 128 may have any shape, size, or form suitable for use in a spinal fusion implant without departing from the scope of the present invention. Also, the number of openings may be varied or no openings may be present on the spinal fusion implant.

Figure 9:
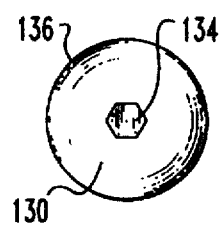
FIG. 9 is a top end view of the spinal fusion implant of FIG. 3.
Figure 8:
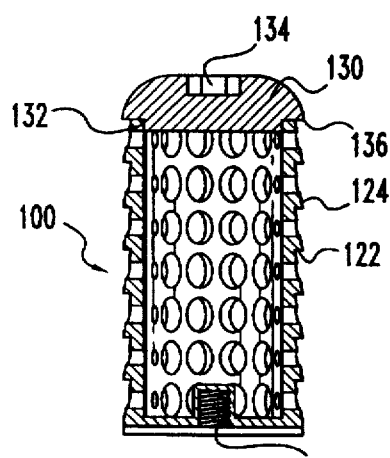
FIG. 8 is a cross sectional view along lines 8—8 of the spinal fusion implant of FIG. 6.

Referring to FIGS. 8 and 9, the spinal fusion implant 100 has a cap 130 with a thread 132 that threadably attaches to one end of the spinal fusion implant 100. Once the cap 130 is attached to the spinal fusion implant 100, the edge 136 acts as an additional ratcheting 120 to further stabilize the spinal fusion implant 100 once it is implanted across the disc space D.

The cap 130 is removable to provide access to the internal chamber 114, such that the internal chamber 114 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 130 and/or the spinal fusion implant 100 itself is made of material appropriate for human implantation such as titanium and/or may be made of, and/or filled and/or coated with a bone ingrowth inducing material such as, but not limited to, hydroxyapatite or hydroxyapatite tricalcium phosphate or any other osteoconductive, osteoinductive, osteogenic, or other fusion enhancing material.

Figure 4:
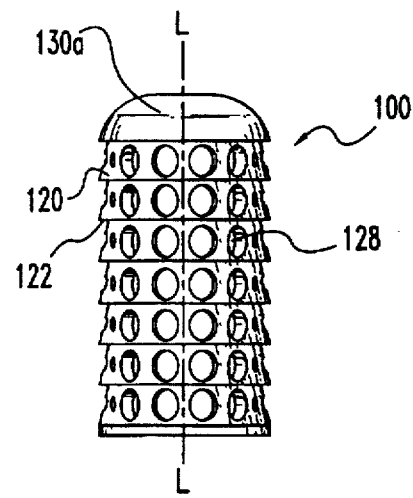
FIG. 4 is a first side elevational view of the spinal fusion implant of FIG. 3.

Referring to FIG. 4, alternatively the cap 130a may be "bullet"-shaped to facilitate insertion. The cap 130a has at its greatest diameter a diameter equal to the root diameter of the spinal fusion implant 100 such that no additional ratchetings 120 are formed.

Figure 10:
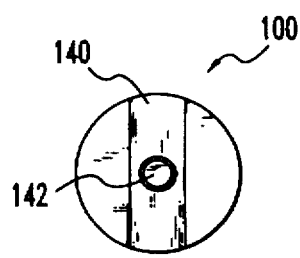
FIG. 10 is a bottom end view of the spinal fusion implant of FIG. 3.

Referring to FIG. 10, the spinal fusion implant 100 has an engagement means at one end in the form of a rectangular slot 140 for engaging a driver instrument having a removable engagement means for intimately engaging the rectangular slot 140. A threaded portion of the driver instrument, which in one embodiment extends as a rod through a hollow tubular member and can be rotationally controlled, screws into a threaded aperture 142 in the slot 140 and binds the implant 100 and the driver instrument together. Once affixed to the implant driver instrument, the spinal fusion implant 100 may be then introduced through a hollow cylindrical tube and driven into the cylindrical hole that has been drilled across the disc space D. The implant driver instrument may then be impacted by a mallet, or similar device, to linearly advance the spinal fusion implant 100 across the disc space D. Once the spinal fusion implant 100 is inserted across the disc space D, the ratchetings 120, engage the bone of the vertebrae V and the implant driver instrument is detached from the spinal fusion implant 100. The procedure for drilling the holes across the disc space D and instrumentation pertaining thereto are described in copending application Ser. No. 08/074,781 filed on Jun. 10, 1993, incorporated herein by reference.

Referring to FIGS. 11–14, an alternative embodiment of the spinal fusion implant of the present invention, generally referred to by the numeral 200 is shown. The spinal fusion implant 200 is similar to the spinal fusion implant 100 except that the openings 228 are bisected by the bone engaging edge 222 of the plurality of ratchetings 220. In this manner, the bone engaging edges are interrupted by the openings 228 to provide a "tooth-like" edge that engages the bone of the vertebrae V and creates an interference fit to prevent the backing out of the implant 200 once inserted. It is appreciated that the number of openings 228 and the number of bone engaging edges 222 may be varied and that the opening 228 can be placed in any orientation relative to the ratchetings 220 or other surface roughening without departing from the scope of the present invention.

Figure 17:
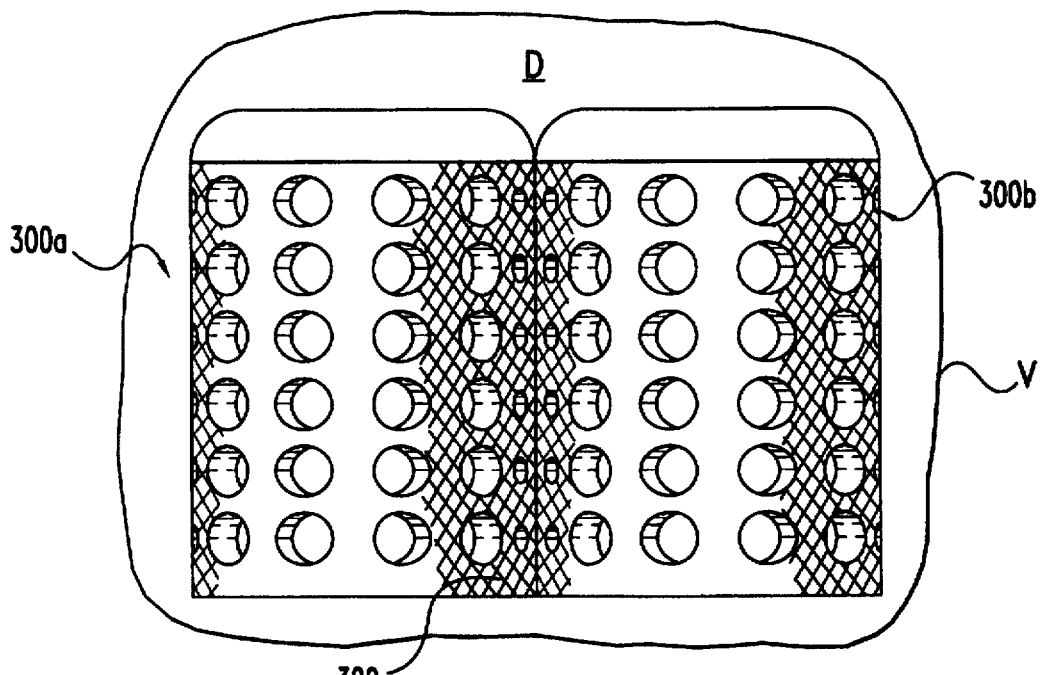
FIG. 17 is a top plan view of two spinal fusion implants of FIG. 15 illustrating the minimum distance possible between the two implant when placed beside each other across the disc space.
Figure 11:
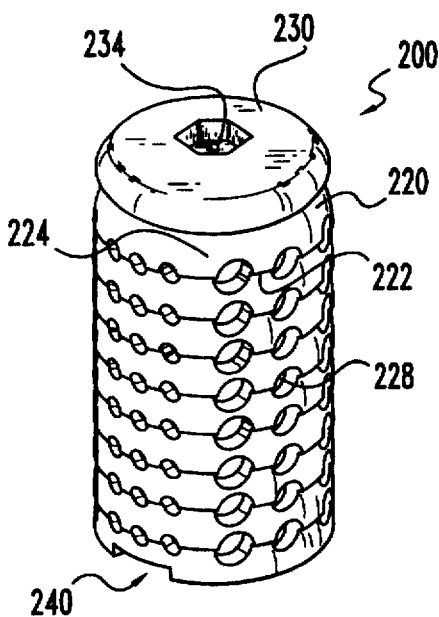
FIG. 11 is a side perspective view of an alternative embodiment of the spinal fusion implant of the present invention.
Figure 12:
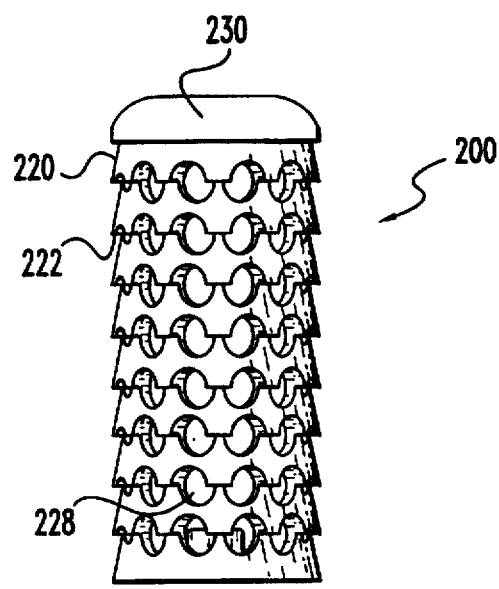
FIG. 12 is a first side elevational view of the spinal fusion implant of FIG. 11.
Figure 14:
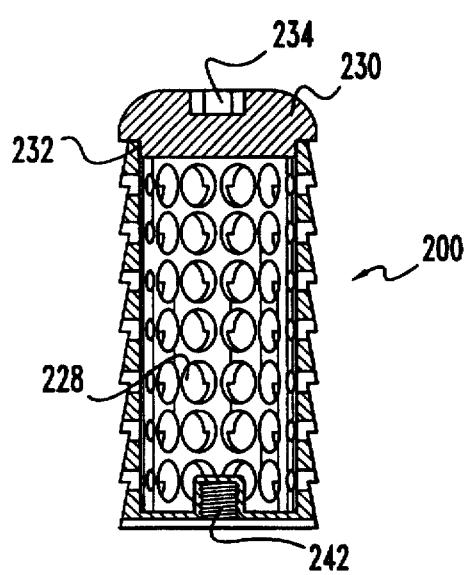
FIG. 14 is cross sectional view along lines 14—14 of the spinal fusion implant of FIG. 13.
Figure 13:
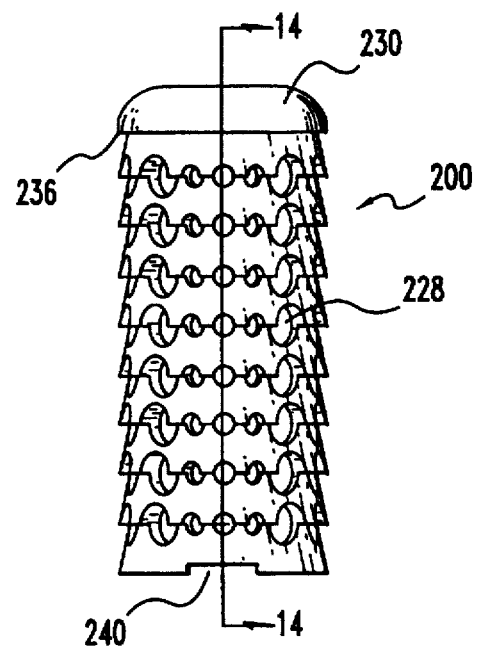
FIG. 13 is a second side elevational view of the spinal fusion implant of FIG. 11.
Figure 15:
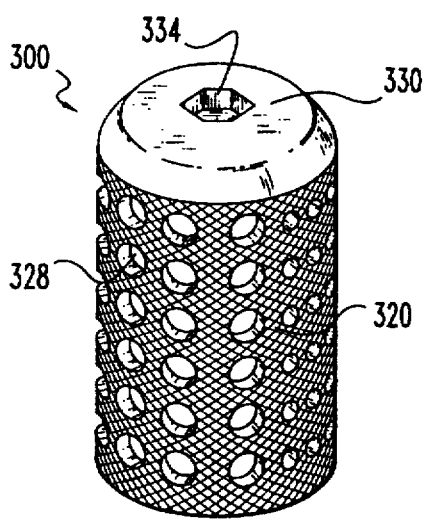
FIG. 15 is a perspective side view of an alternative embodiment of the spinal fusion implant of the present invention having surface roughenings in the form of knurling.
Figure 16:
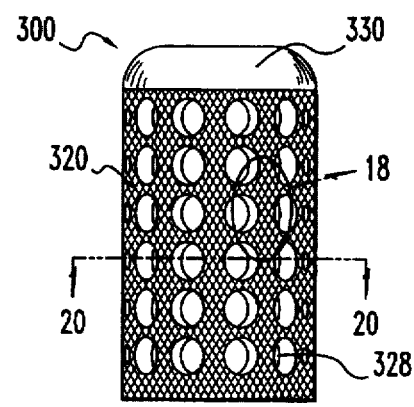
FIG. 16 is a first side elevational view of the spinal fusion implant of FIG. 15.
Figure 20:
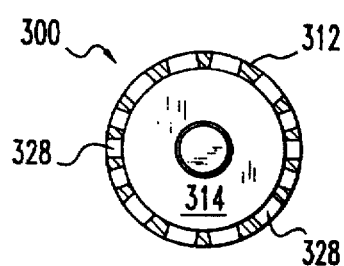
FIG. 20 is a cross sectional view along lines 20—20 of the spinal fusion implant of FIG. 16.
Figure 21:
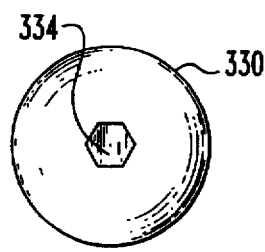
FIG. 21 is a top end view of the spinal fusion implant of FIG. 15.
Figure 22:
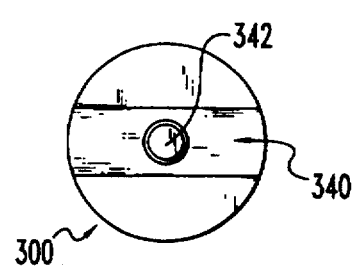
FIG. 22 is a bottom end view of the spinal fusion implant of FIG. 15.
Figure 18:
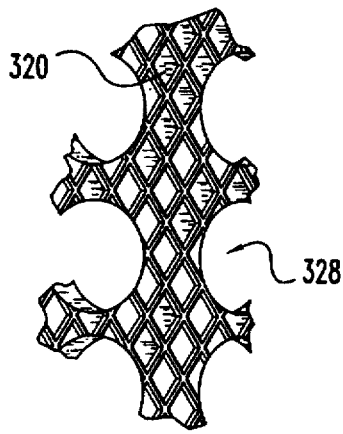
FIG. 18 is an enlarged fragmentary view along line 18 of FIG. 16 showing the surface configuration of the implant of FIG. 15.
Figure 19:
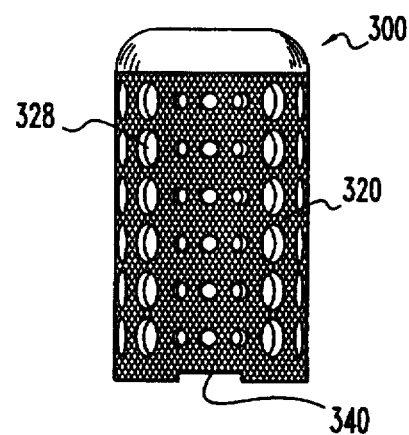
FIG. 19 is a second side elevational view of the spinal fusion implant of FIG. 15.

Referring to FIGS. 15–19, an alternative embodiment of the spinal fusion implant of the present invention generally referred to by the numeral 300 is shown. The spinal fusion implant 300 has a substantially cylindrical configuration having surface rougheings for stabilizing the implant 300 within the intervertebral space D. As shown in FIG. 18, the surface rougheings comprise a surface knurling 320 such as, but not limited to, the diamond-shaped bone engaging pattern shown. The spinal fusion implant 300 may have surface knurling 320 throughout the entire external surface of the spinal fusion implant 300, throughout only a portion of the external surface, or any combination thereof, without departing from the scope of the present invention. In those circumstances where there is no undrilled bone in the disc space D forward of the spinal fusion implant 300 to resist further forward advancement of the implant, surface knurling 320 is preferred as it produces an exceedingly high interference fit with the bone of the vertebrae V and resists motion equally in all directions and without the tendency to urge itself forward.

Referring to FIG. 17, two spinal fusion implants 300a and 300b may be placed side by side across the disc space D having the same dimensions of the disc space D shown in FIG. 2, such that the two spinal fusion implants 300a and 300b are touching each other and thus reducing the overall combined width of the two spinal implants 300a and 300b to the minimum distance possible with a substantially cylindrical implant having a roughened surface. In this manner, two cylindrical spinal fusion implants 300a and 300b having a sufficient diameter to cross the height $H_S$ of the disc space D can be placed across the disc space D without exceeding the transverse width $W_S$ of the spinal column S. The spinal fusion implants 300a and 300b are inserted by linear advancement as described above for spinal fusion implant 100. Therefore, as no threading is required for the insertion of spinal fusion implants 300a and 300b, little or no space need be present between the spinal fusion implants 300a and 300b, as compared to the space that would be required for a thread when using threaded implants. Thus, the spinal fusion implants 300a and 300b may be placed closer together to substantially reduce the overall combined width of two such implants.

Referring to FIGS. 23–30, an alternative embodiment of the spinal fusion implant of the present invention is shown and is generally referred to by the numeral 400. The spinal fusion implant 400 has a similar configuration to that of the spinal fusion implant 200, except that it comprises a partially cylindrical member having arcuate portions 402 and 404 which are arcs of the same circle with portions of its outer wall 405 that are flattened so as to present a first flat side 406 and a second flat side 408.

Figure 28:
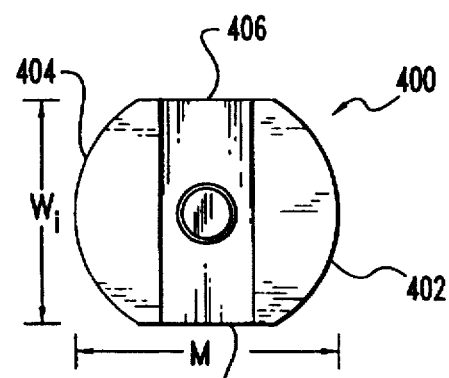
FIG. 28 is a bottom end view of the spinal fusion implant of FIG. 23.

Referring to FIG. 28, the spinal fusion implant 400 has a major diameter M equal to the distance between two diametrically opposite non-flattened segments, such as arcuate portions 402 and 404 which are arcs of the same circle. The width $W_i$ of the spinal fusion implant 400 is equal to the distance between a flattened segment and a point diametrically opposite the flattened segment, such as the distance between the first and second flat sides 406 and 408.

Figure 25:
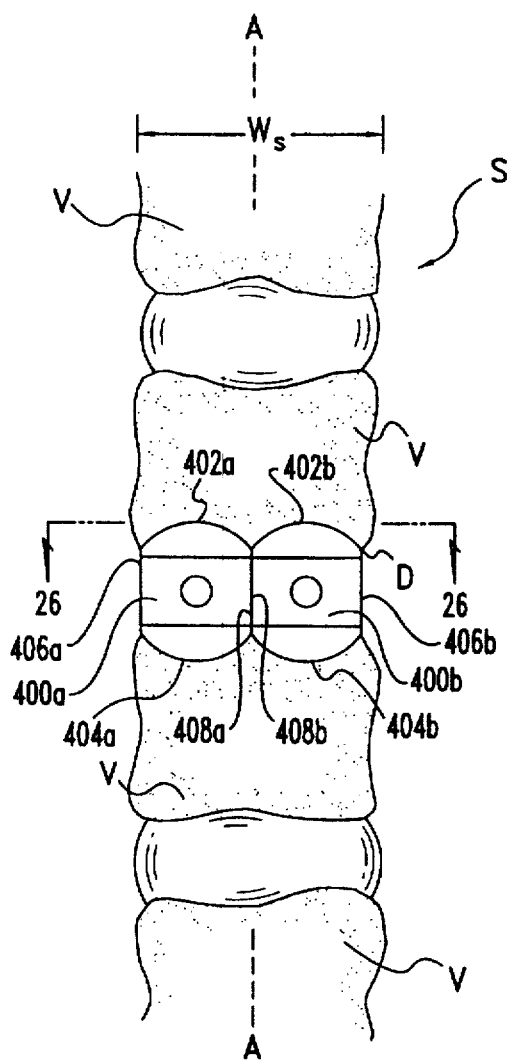
FIG. 25 is a diagrammatic representation of a segment of the human spinal column showing two implants of FIG. 23 the present invention inserted within the spine.

Referring to FIG. 25, a diagrammatic representation of a segment of a spinal column S comprising several vertebrae V is shown having two spinal fusion implants 400a and 400b inserted across the disc space D between the two adjacent vertebrae V. The spinal fusion implants 400a and 400b are identical and each has a first arcuate portion 402a and 402b, respectively; a second arcuate portion 404a and 404b, respectively; a first flat side 406a and 406b, respectively; and a second flat side 408a and 408b, respectively. The spinal fusion implants 400a and 400b are implanted across the disc space D with the second flat side 408a of spinal fusion implant 400a facing and adjacent to the first flat side 408b of spinal fusion implant 400b such that the combined overall width of the two spinal fusion implants 400a and 400b is less than twice the maximum diameter M of the implants. The spinal fusion implants 400a and 400b are inserted by linear advancement as described above for spinal fusion implant 100.

Prior to implantation, two partially overlapping cylindrical holes are drilled across the disc space D and into the adjacent vertebrae V. The holes are drilled sufficiently overlapping to allow the two spinal fusion implants 400a and 400b to be implanted with the flat sides perpendicular to the plane of the disc space D, the disc space D being in a plane perpendicular to the longitudinal vertical axis A of the spinal column S as shown in FIG. 25.

The spinal fusion implants 400a and 400b may be inserted separately such that once a first spinal fusion implant 400a is inserted across the disc space D, a second spinal fusion implant 400b is driven across the disc space D so that the flat side 402 or 404 of each spinal fusion implant 400 are adjacent to each other and are touching. In this manner, the two spinal fusion implants 400a and 400b are implanted across the disc space D and engage the bone of the adjacent vertebrae V without exceeding the transverse width $W_S$ of the spinal column S. Alternatively, the two spinal fusion implants 400a and 400b may be implanted across the disc space D simultaneously by placing them adjacent and facing each other, in the orientation described above, prior to implantation. The two spinal fusion implants 400a and 400b are then linearly advanced into the drilled holes across the disc space D.

Referring to FIG. 28, the effect of having first and second flat sides 406 and 408 is that the overall width $W_i$ of the spinal fusion implant 400 is substantially reduced while the height of the spinal fusion implant 400 remains the maximum diameter M of the cylindrical portion of the spinal fusion implant 400.

Figure 26:
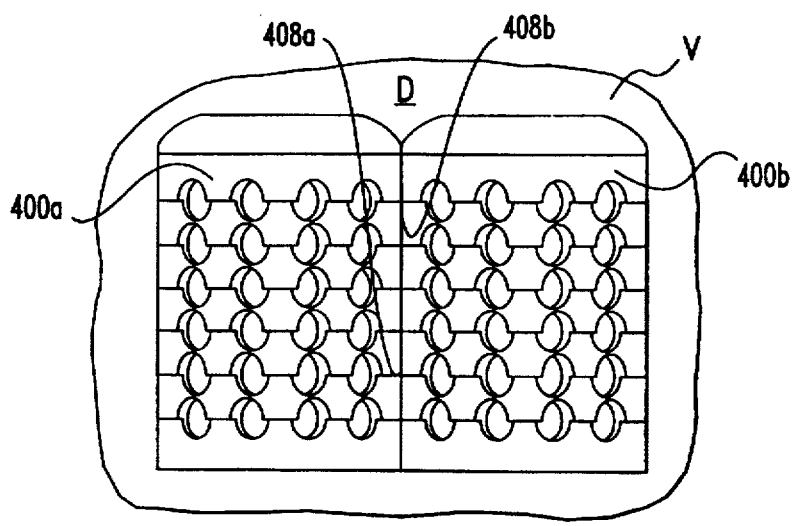
FIG. 26 is a top plan view along lines 26—26 of FIG. 25 with the top vertebrae removed, illustrating the minimum distance possible between two spinal fusion implants of FIG. 23 placed beside each other across the disc space.

Referring to FIGS. 25 and 26, as the height of each spinal fusion implant 400a and 400b is sufficient to cross the disc space D and into the two adjacent vertebrae V, each spinal fusion implant 400a and 400b engages the bone of the adjacent vertebrae V while the combined width of the two spinal fusion implant 100 does not exceed the transverse width $W_S$ of the spinal column S. As a result, the advantages of placing two cylindrical implants side by side across the disc space D may be obtained without exceeding the width $W_S$ of the spinal column S. Thus, as shown in FIG. 26, the two spinal fusion implants 400a and 400b can be inserted across the disc space D, having the same dimensions as the disc space D shown in FIG. 2, and can be placed much closer together as a result of the first flat side 408b placed adjacent to the second flat side 408a while continuing to engage the adjacent vertebrae V.

Figure 30A:
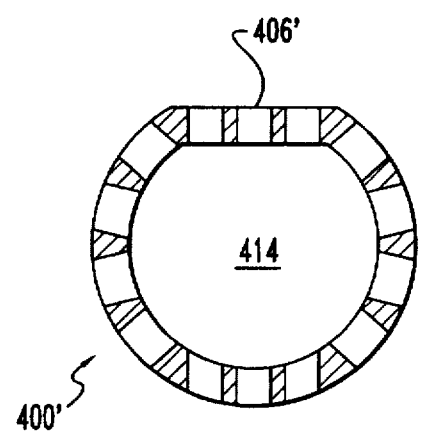
FIG. 30A is cross sectional view of an alternative embodiment of the spinal fusion implant of the present invention having only one flat side.
Figure 30:
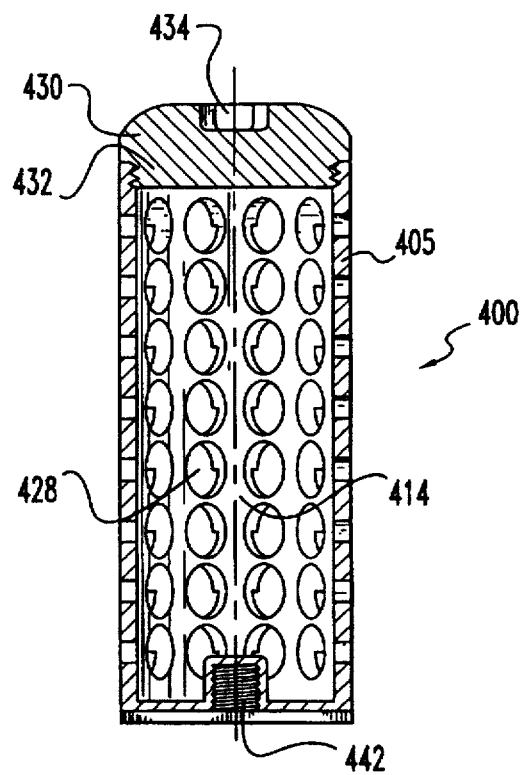
FIG. 30 is a cross sectional view along lines 30—30 of the spinal fusion implant of FIG. 29.
Figure 31:
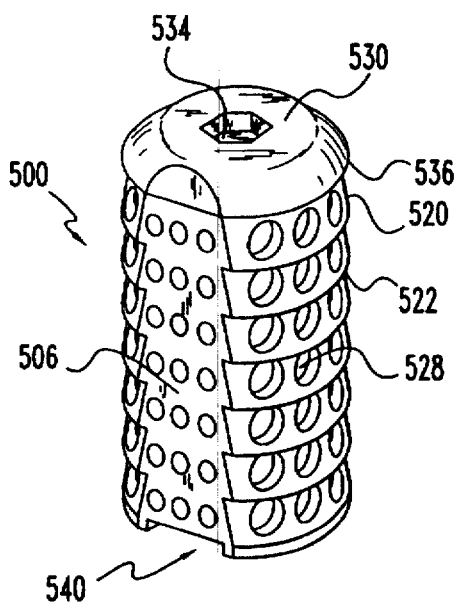
FIG. 31 is a perspective side view of an alternative embodiment of the spinal fusion implant of the present invention having flat sides and surface roughenings in the form of ratchetings.
Figure 32:
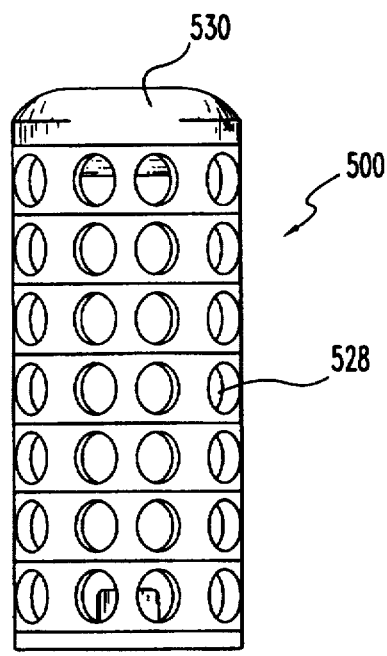
FIG. 32 is a first side elevational view of the spinal fusion implant of FIG. 31.
Figure 35:
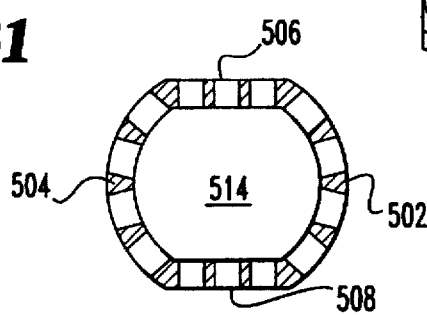
FIG. 35 is a cross sectional view along lines 35—35 of the spinal fusion implant of FIG. 33.
Figure 34:
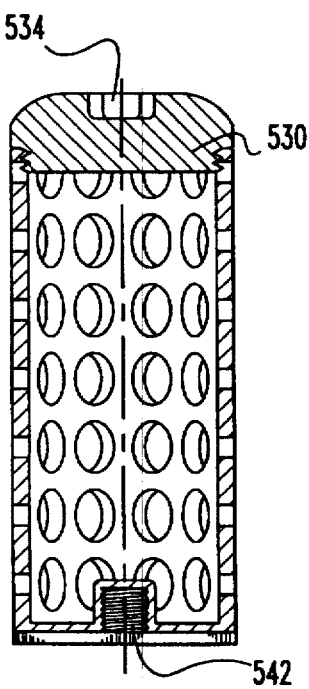
FIG. 34 is a cross sectional view along lines 34—34 of the spinal fusion implant of FIG. 33.
Figure 33:
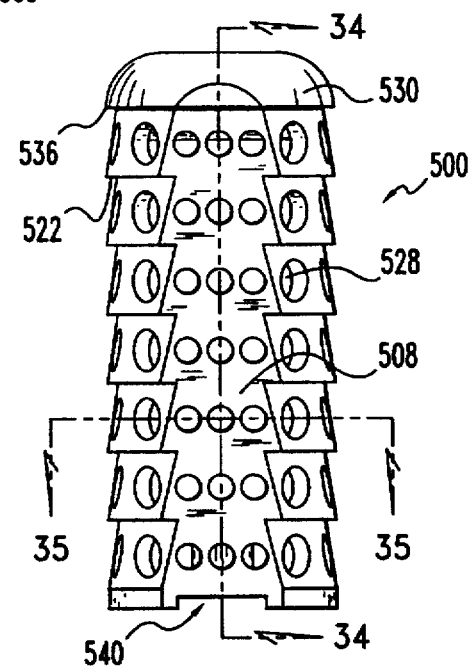
FIG. 33 is a second side elevational view of the spinal fusion implant of FIG. 31.

As shown in FIG. 30, the spinal fusion implant 400 has a hollow internal central chamber 414 and has a series of openings 428 passing through the outer wall 405 and into the central chamber 414 of the spinal fusion implant 400. The openings 428 may also be present on the first and second flat sides 406 and 408. Said openings 428 while shown as round holes for example, may be any other workable configuration consistent with their purpose and may include, but is not limited to, ovals, slots, grooves and holes that are not round as is true for any of the cylindrical implants disclosed above.

Referring to FIG. 30A, it is appreciated that it is also within the scope of the present invention that the spinal fusion implant 400' could have only one flat side so as to provide only a first flat side 406'. This configuration is appropriate where the width $W_i$ of the spinal fusion implant 400 need only be slightly reduced with respect to its maximum diameter M, to prevent the combined overall width of two such implants from exceeding the transverse width $W_S$ of the spinal column S.

Figure 23:
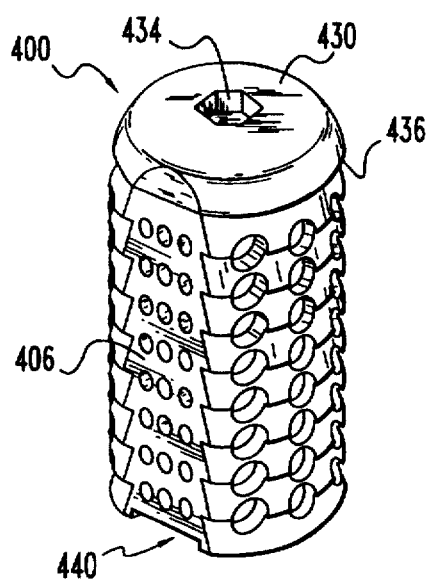
FIG. 23 is a perspective side view of an alternative embodiment of the spinal fusion implant of the present invention having flat sides and surface roughenings in the form of ratchetings.
Figure 24:
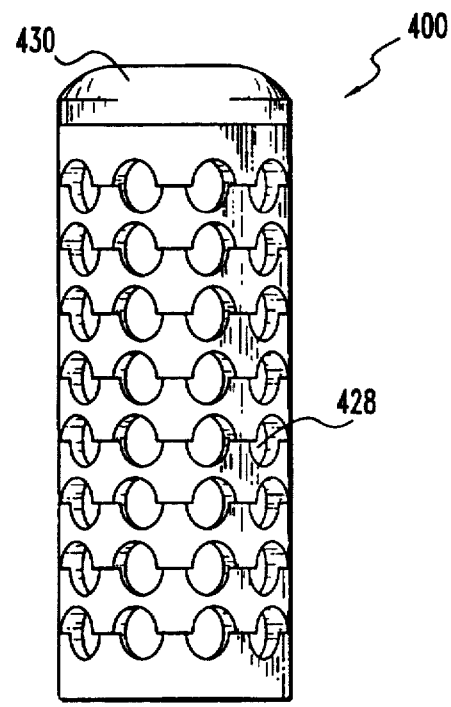
FIG. 24 is a first side elevational view of the spinal fusion implant of FIG. 23.
Figure 29:
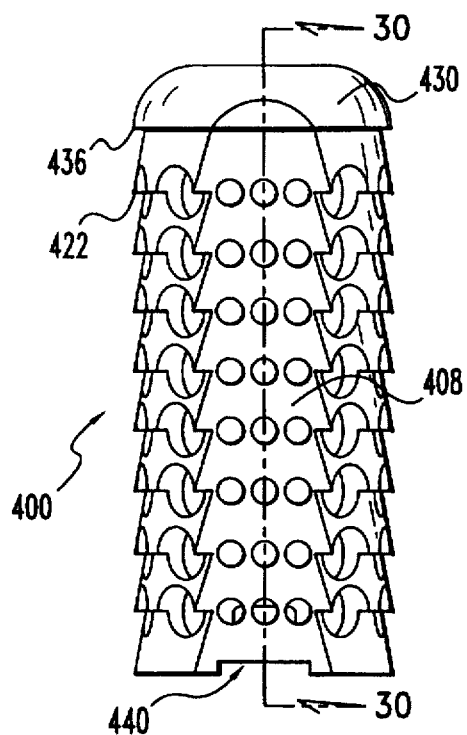
FIG. 29 is a second side elevational view of the spinal fusion implant of FIG. 23.

Referring to FIGS. 23, 24, and 29, the spinal fusion implant 400 of the present invention has a plurality of ratchetings 420 facing one direction, as described above for spinal fusion implant 100, along the outer surface of the cylindrical portion of the circumference of the spinal fusion implant 400. The ratchetings 420 have a bone engaging edges 422 and the angled configuration of the ratchetings 420 provide for a "one-way" insertion of the spinal fusion implant 400 as the movement of the spinal fusion implant 400 in the opposite way is prevented by the engagement or the engaging edges 422 with the vertebrae V. However, the flat sides 402 and 404 are preferably smooth and have a flat surface so as to allow placement in the closest possible proximity of the two spinal fusion implants 400a and 400b. The bone engaging edge 422 of each ratcheting 420 bisects the holes 428 to increase the stability of the spinal fusion implant 400 once implanted.

The spinal fusion implants 100–600 each have an overall length in the range of 20 mm to 30 mm, with 25 mm being preferred, and a maximum diameter X in the range of 14 mm to 24 mm, with 18 mm being preferred when inserted in the lumbar spine from the posterior approach, and 20 mm being preferred when inserted in the lumbar spine from the anterior approach. The spinal fusion implant 400 is quite appropriate for use in the cervical and thoracic spine as well. In the cervical spine such implants would have a length in the range of 10–18 mm preferred 12 mm and a maximum diameter M in the range of 12–20 mm, with the preferred diameter being 16 mm. In the thoracic spine such implants would have, a length in the range of 16–26 mm and a greatest diameter in the range of 14–20 mm, with the preferred diameter being 16 mm. In addition to the foregoing dimensions, spinal fusion implants 400–600 have a width $W_i$ for use in the cervical spine in the range of 8–26 mm, with the preferred width $W_i$ being 10–14 mm; for use in the lumbar spine in the range of 18–26 mm, with the preferred width $W_S$ being 18–20 mm; and for use in the lumbar spine in the range of 18–26 mm, with the preferred width $W_i$ being 20–24 mm.

Figure 27:
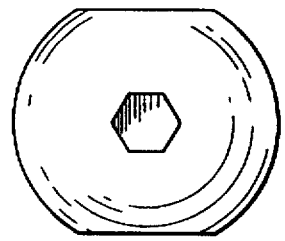
FIG. 27 is a top end view of the spinal fusion implant of FIG. 23.

Referring to FIGS. 27 and 28, when viewed on end, the spinal fusion implant 400 of the present invention has externally the geometrical configuration of a circle with a portion of each side tangentially amputated vertically to form the first and second flat sides 406 and 408. The cap 430 extends beyond the narrowest diameter of the wall 412 along the first and second arcuate portions 402 and 404 at the end of the spinal fusion implant 400 and acts as an additional ratcheting 420 with an engaging edge 436. In this manner, the additional ratcheting 420 functions to further increase the stability of the spinal fusion implant 400 once inserted between the adjacent vertebrae V and to further prevent the dislodgement of the spinal fusion implant 400 from the disc space D. The cap 430 is flush with the flat sides 406 and 408 to preserve the flat surfaces of flat sides 406 and 408. The cap 430 further has a sloping sides 438a and 438b corresponding position with the flat sides 406 and 408 to facilitate insertion of the spinal fusion implant 400 and to permit for close side by side placement of two spinal fusion implants 400. Alternatively, the cap 430 can be flush all the way around with the root diameter of the spinal fusion implant 400 to further facilitate insertion for a longer ramp length.

The spinal fusion implant 400 has surface roughenings such as, but not limited to, ratchetings 420 such that the outer surface of the spinal fusion implant 400 may have a plurality of other surface roughenings to enhance the stability of the spinal fusion implant 400 and to resist dislodgement once implanted across the disc space D. For example, the spinal fusion implant 400 may have an irregular outer surface that may be created by blasting or rough casting and the like. Such an irregular surface may be used alone or in combination with other surface roughenings such as ratchetings and/or knurling and as already discussed, the openings 428 may be holes, grooves, slots or other.

Referring to FIGS. 32–35, an alternative embodiment of the spinal fusion implant of the present invention is shown and generally referred to by the numeral 500. The spinal fusion implant 500 is substantially the same as the spinal fusion implant 400, except that the openings 528 are positioned on the ratcheting 520 such that the openings 528 are positioned between the bone engaging edges 522 and are not bisected by the bone engaging edges 522. In this manner the bone engaging edges 522 are continuous and uninterrupted to engage the bone of the vertebrae V and prevent the backing out of the implant 500 once inserted.

Referring to FIG. 36–40, an alternative embodiment of the spinal fusion implant of the present invention is shown and generally referred to by the numeral 600. The spinal fusion implant 600 is substantially identical to the spinal fusion implant 400 described above except that in place of ratchetings 420, it has surface knurling 620 such as, but not limited to, the diamond-shaped bone engaging pattern shown in FIG. 40. The surface knurling 620 assists in the retaining of the spinal fusion implant 600 once it is inserted across the disc space D between two adjacent vertebrae V. It is recognized that the surface knurling 620 of the implant 600 may be combined with any of a number of other surface roughenings such as, but not limited to, ratchetings to assist in retaining the spinal fusion implant 600 across the disc space D.

Figure 36:
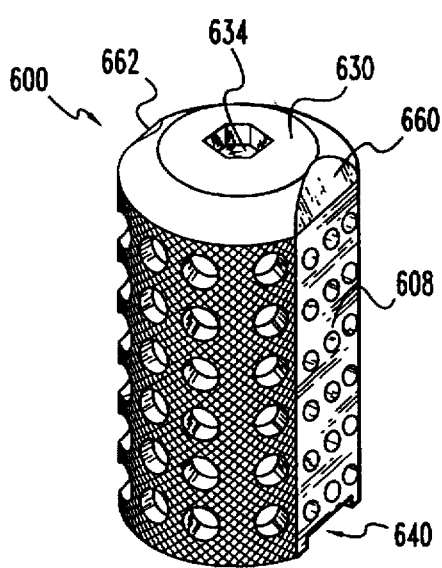
FIG. 36 is a perspective side view of an alternative embodiment of the spinal fusion implant of the present invention having flat sides and having surface roughenings in the form of knurlimg.
Figure 37:
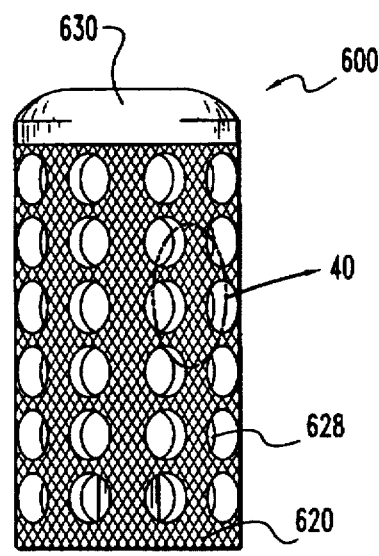
FIG. 37 is a first side elevational view of the spinal fusion implant of FIG. 36.
Figure 39:
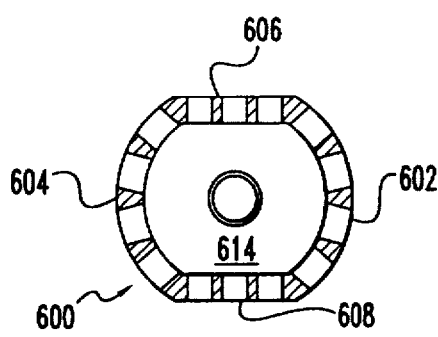
FIG. 39 is a cross sectional view along lines 39—39 of the spinal fusion implant of FIG. 38.
Figure 40:
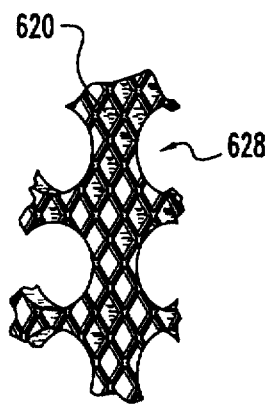
FIG. 40 is an enlarged fragmentary view along line 40 of FIG. 37 showing the surface configuration of the spinal fusion implant of FIG. 36.
Figure 38:
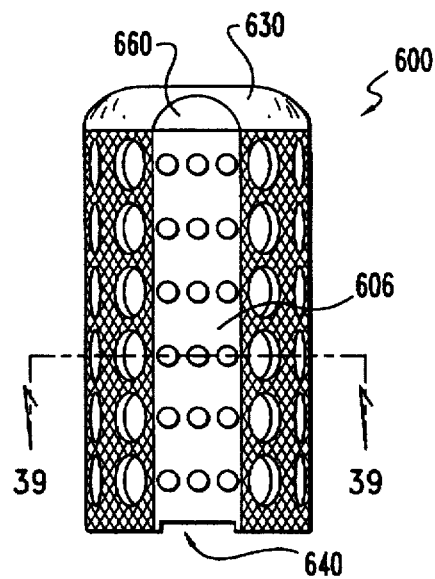
FIG. 38 is a second side elevational view of the spinal fusion implant of FIG. 36.

As shown in FIG. 36, the cap 630 of the spinal fusion implant 600 has sloping sides 660 and 662 corresponding with the first and second flat sides 606 and 608 to facilitate insertion of the spinal fusion implant 600 and to permit for close side by side placement of two spinal fusion implants 600.

It is appreciated that the implant invention may include any and all surface roughening configuration that either increase the surface area or interference fit of the implant and the vertebrae V. It is appreciated that the ratchetings described above for the various embodiments of the spinal fusion implants of the present invention may also comprise a knurled or other surface roughenings in combination with the ratchetings to further enhance the retention of the spinal fusion implant across the disc space D once inserted.

Figure 41:
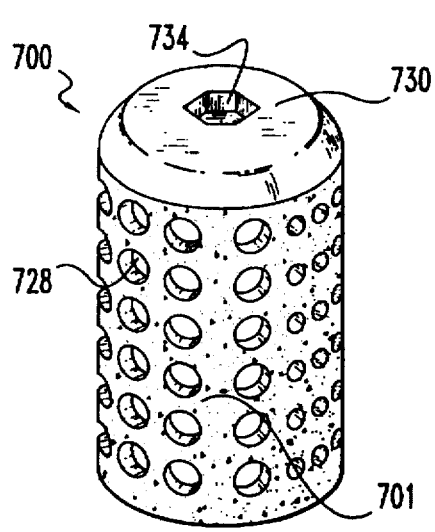
FIG. 41, is a perspective side view of an alternative embodiment of the spinal fusion implant of the present invention having surface roughenings comprising of a blasted external surface.

Referring to FIG. 41, an alternative embodiment of the spinal fusion implant of the present invention generally referred to by the numeral 700 is shown. The spinal fusion implant 700 has surface roughenings comprising of a blasted external surface 701 to provide an engagement surface for the vertebrae V when inserted across the disc space D. The spinal fusion implant has a plurality of openings 728, a removable cap 730 with a hex slot 734 for engaging a hex tool.

Figure 42:
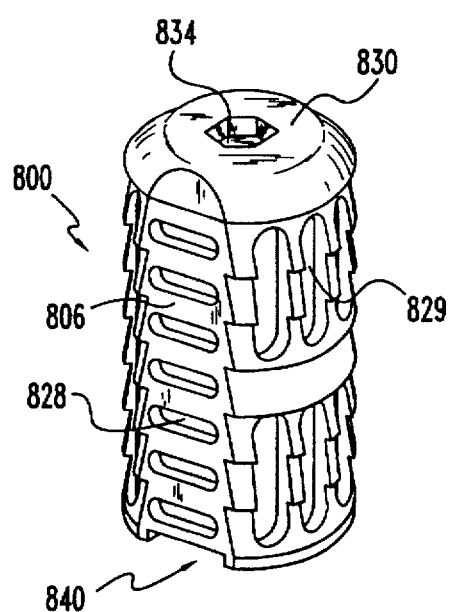
FIG. 42 is a perspective side view of an alternative embodiment of the spinal fusion implant of the present invention having flat sides and openings in the form of vertical and horizontal slots.

Referring to FIG. 42, an alternative embodiment of the spinal fusion implant of the present invention generally referred to by the numeral 800 is shown. The spinal fusion implant 800 is similar to spinal fusion implant 400 described above except that it has openings in the form of horizontal slots 828 on the flat side 806 and vertical slots 829 on the cylindrical portion of the spinal fusion implant 800.

It is appreciated that the spinal implants of the present invention may have any configuration such that the combined overall width of the two such spinal fusion implants is less than twice the maximum diameter M of those implants without departing from the scope of the present invention.

Figure 43:
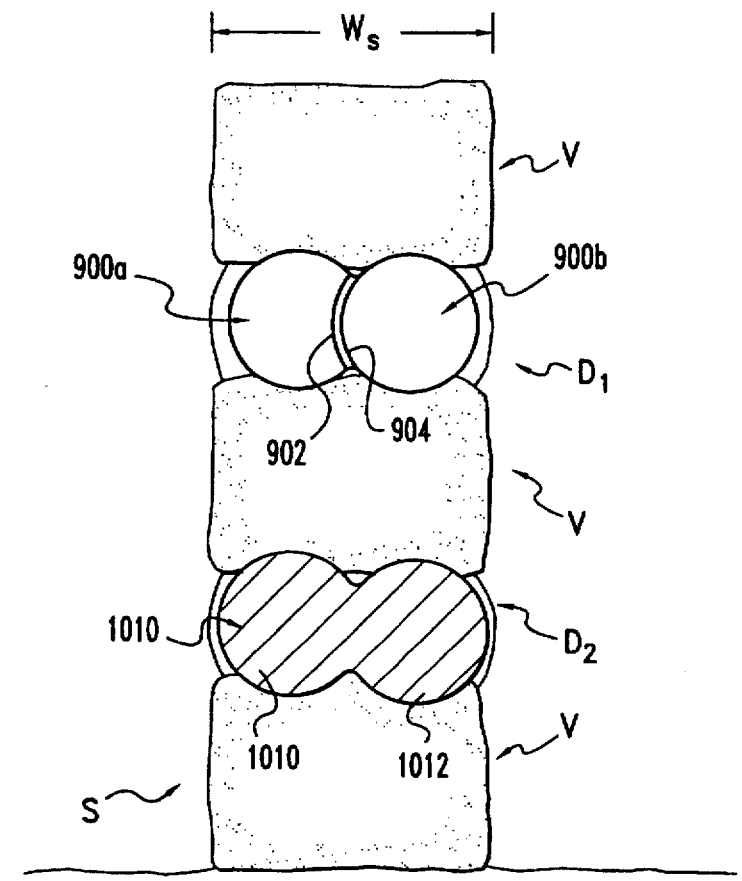
FIG. 43 is an elevational side view of a segment of the spinal column with an alternative embodiment of two spinal fusion implants of the present invention having corresponding concave and convex sides inserted across one disc space and an alternative embodiment of a single spinal fusion implant of the present invention having a two cylindrical portions inserted across one disc space.

Referring to FIG. 43, a segment of the spinal column S is shown with an alternative embodiment of two spinal fusion implants 900a and 900b inserted across disc space $D_1$ is shown. Spinal fusion implant 900a has a concave surface 902 which is correspondingly shaped for receiving the convex surface 904 of spinal fusion implant 900b. When the two spinal fusion implants 900a and 900b are placed side by side, the concave surface 902 mates with the convex surface 904 such that the combined overall width of the two spinal fusion implants is less than twice the maximum diameter M of those implants. As a result, the advantages of placing two implants that are partially cylindrical, with respect to the portion engaging the vertebrae V, side by side across the disc space D may be obtained without exceeding the width $W_S$ of the spinal column S.

Referring still to FIG. 43, an alternative embodiment of the spinal fusion implant of the present invention comprising a single spinal fusion implant 1000 inserted across the disc space $D_2$ of the spinal column S is shown. The spinal fusion implant 1000 comprises a first cylindrical portion 1010 and a second cylindrical portion 1012 and may have any of the surface roughenings described above in reference to the embodiments set forth above. In the preferred embodiment, the spinal fusion implant 1000 is inserted by linear advancement into two overlapping cylindrical holes drilled across the disc space $D_2$.

While the present invention has been described in detail with regard to the preferred embodiments, it is appreciated that other variations of the present invention may be devised which do not depart from the inventive concept and scope of the present invention.

What is claimed is:

1. A method for inserting a plurality of partially cylindrical non-threaded spinal fusion implants made of a material appropriate for human implantation, each of said plurality of implants comprising a cylinder having a longitudinal central axis and at least one flat side parallel to said central axis, said implant having a maximum diameter larger than the disc space between two adjacent vertebrae, comprising the steps of:

drilling two partially overlapping cylindrical holes across the disc space between the two adjacent vertebrae;

pushing a first of said partially cylindrical spinal fusion implants having a first flat side into one of said overlapping cylindrical holes, said first flat side being oriented perpendicular to the plane of said disc space;

pushing a second of said partially cylindrical implants having a second flat side into a second of said overlapping holes, said second flat side being adjacent and facing said first flat side of said first implant.

2. A method for inserting a plurality of partially cylindrical non-threaded spinal fusion implants made of a material appropriate for human implantation, each of said plurality of implants comprising a cylinder having a longitudinal central axis and at least one flat side parallel to said central axis, said implant having a diameter larger than the disc space between two adjacent vertebrae, said disc space being in a plane perpendicular to the longitudinal vertical axis of the spinal column, comprising the steps of:

drilling two partially overlapping cylindrical holes across the disc space between the two adjacent vertebrae;

pushing a first of said partially cylindrical spinal fusion implants having a first flat side into one of said overlapping cylindrical holes, said first flat side being oriented perpendicular to the plane of said disc space;

pushing a second of said partially cylindrical implants having a second flat side into a second of said overlapping holes, said second flat side being adjacent and facing said first flat side of said first implant.

3. A partially cylindrical spinal fusion implant made of a material appropriate for human implantation, said spinal fusion implant comprising a partially cylindrical non-threaded body portion having an exterior surface formed by opposite cylindrical portions defining a maximum diameter and intermediate opposite non-cylindrical portions defining a width therebetween configured to be placed in close proximity to a second partially cylindrical non-threaded spinal fusion implant, whereby said first and second implants when placed together said non-cylindrical portions in proximity have a combined overall width that is less that than the sum of the individual maximum diameters of each of said first and second implant implants.

4. The fusion implant of claim 3 wherein at least one of said opposite non-cylindrical portions is substantially flat.

5. The partially cylindrical spinal fusion implant of claim 3, wherein at least one of said opposite cylindrical portions includes surface roughenings.

6. The partially cylindrical spinal fusion implant of claim 5, wherein said surface roughenings includes ratchetings.

7. The partially cylindrical spinal fusion implant of claim 3, wherein at least one of said opposite cylindrical portions includes a number of openings therethrough sized to contain bone fusion promoting material.

8. A method for inserting a plurality of spinal fusion implants made of a material appropriate for human implantation, at least one of the plurality of implants having the form of a partial cylinder with a first longitudinal central axis with a portion of the external surface being concave and another of the implants having the form of a complete cylinder with a second longitudinal central axis wherein the largest diameter of the partial cylinder and the diameter of the complete cylinder are each larger than the disc space between two adjacent vertebrae, comprising the steps of:

drilling two partially overlapping cylindrical holes across the disc space between the two adjacent vertebrae;

inserting the partially cylindrical spinal fusion implant having a non-cylindrical portion which is concave into one of the overlapping cylindrical holes, the concave portion being oriented such that the concave portion will substantially lie on an arc defined by the radius of the second cylindrical hole adjacent; and inserting the completely cylindrical implant into the second of said overlapping holes with the implant in close proximity to the concave portion of the first implant.

9. A partially cylindrical spinal fusion implant made of a material appropriate for human implantation, said spinal fusion implant comprising:

a first fusion implant having a longitudinal central axis, a first non-threaded cylindrical portion having a first diameter and at least one non-cylindrical portion with an external surface oriented at a distance transverse from said longitudinal central axis that is less than the distance of the cylindrical portion from the longitudinal axis; and a second body having a second cylindrical portion with a second diameter;

wherein the second implant is capable of being placed in close proximity to said non-cylindrical portion of said first spinal fusion implant to produce a combined overall width that is less than the sum of the first and second diameters.

10. The partially cylindrical spinal fusion implant of claim 9 wherein said nonm-cylindrical portion is substantially flat.

11. The partially cylindrical spinal fusion implant of claim 9, wherein at least one of said first and second cylindrical portions includes surface roughenings.

12. The partially cylindrical spinal fusion implant of claim 11, wherein said surface roughenings includes ratchetings.

13. The partially cylindrical spinal fusion implant of claim 9, wherein at least one of said first and second cylindrical portions includes a number of openings therethrough sized to contain bone fusion promoting material.

* * * * *